(12) United States Patent
Ohtsuki et al.

(10) Patent No.: US 6,296,748 B1
(45) Date of Patent: Oct. 2, 2001

(54) GAS SENSOR

(75) Inventors: Shoich Ohtsuki; Satoshi Ishikawa, both of Komaki (JP)

(73) Assignee: NGK Spark Plug Co., Ltd., Nagoya (JP)

( * ) Notice: Subject to any disclaimer, the term of this patent is extended or adjusted under 35 U.S.C. 154(b) by 0 days.

(21) Appl. No.: 09/377,619

(22) Filed: Aug. 19, 1999

(30) Foreign Application Priority Data

Aug. 19, 1998 (JP) .................................................. 10-232701

(51) Int. Cl.[7] .................................................. G01N 27/407
(52) U.S. Cl. ........................... 204/427; 204/424; 204/428
(58) Field of Search ...................................... 204/421–429

(56) References Cited

U.S. PATENT DOCUMENTS

| | | | |
|---|---|---|---|
| 4,152,232 | * 5/1979 | Otsuka et al. | 204/428 |
| 5,246,562 | * 9/1993 | Weyl et al. | 204/424 |
| 5,573,650 | * 11/1996 | Fukaya et al. | 204/424 |
| 5,679,226 | 10/1997 | Furusaki et al. | |
| 5,695,625 | * 12/1997 | Yamada et al. | 204/428 |
| 5,785,829 | 7/1998 | Watanabe . | |
| 5,900,129 | * 5/1999 | Tsuji et al. | 204/427 |

FOREIGN PATENT DOCUMENTS

| | | |
|---|---|---|
| 702229 A1 | 3/1996 | (EP) . |
| 899562 A2 | 3/1999 | (EP) . |

* cited by examiner

Primary Examiner—T. Tung
(74) Attorney, Agent, or Firm—Morgan, Lewis & Bockius LLP

(57) ABSTRACT

A gas sensor is provided which can efficiently flow air into a casing while having a sufficient on-axis sectional area in a ceramic separator for allowing lead wires to pass therethrough. The oxygen sensor has a ceramic separator main body portion axially formed with a plurality of separator-side lead wire insertion holes penetrating therethrough, whereby a first part thereof is arranged to extend to an inner side of a filter support portion. The first part has an on-axis sectional outer shape formed in a shape other than a circle, e.g. a polygonal shape, such as a square shape. By making the on-axis sectional outer shape of the ceramic separator main body part non-circular as above, it is possible to locally expand a gap defined between an outer peripheral surface of the ceramic separator and an inner surface of the filter support portion. This makes it possible to efficiently flow external air into the casing while providing the ceramic separator with a sufficient on-axis sectional area for passing through lead wires.

8 Claims, 14 Drawing Sheets

GAS SENSOR

This application claims the benefit of Japanese Patent Application No. Hei 10-232701, which is hereby incorporated by reference.

BACKGROUND OF THE INVENTION

1. Field of the Invention

The invention relates to a gas sensor, such as an oxygen sensor, HC sensor, NOx sensor, etc., which measures a gas introduced into the sensor and detects a component of the gas.

2. Description of the Related Art

Conventional gas sensors have a metal casing, inside which resides a detection element formed in a bar-like or cylindrical shape and having, at a tip, a detecting section to detect a component gas. For a gas sensor using air as a reference gas, e.g. an oxygen sensor, it is necessary to provide a portion for introducing air into the casing and accommodating a detection element or providing a filter support cylinder coupled to a rear end of the casing. This type of air introducing element can be formed, for example, by opening a gas passage hole in a rear end side wall of the casing or filter support cylinder and covering it with a water repellent filter. Meanwhile, an air introducing element may be provided by a lead wire insertion hole formed in a rubber grommet sealing lead wire extension port. This method introduces air into a casing through a gap formed between a coat material covering a lead-wire outer surface and a lead wire insertion hole.

In some conventional structures as described above, a ceramic separator formed with a lead wire insertion hole is provided in a casing (or filter support cylinder) in order to prevent a short circuit between lead wires extending from a detection element and heater. This ceramic separator is formed in a cylindrical shape matched to the casing, and is usually arranged at a rear end inside of the casing (or filter support cylinder) in order to be positioned on a side to extend a lead wire therefrom. On the other hand, an air introducing element as above is formed at the casing (or filter support cylinder) rear end, and a gap is provided between an outer peripheral surface and an inner peripheral surface of the casing (or filter support cylinder), in many cases, to provide a passage for the introduced air. However, recently there has been a movement toward reducing the size of the sensor, and, thus, there is an effort to reduce the diameter of the casing (or filter support cylinder) as small as possible. Thus, due to this effort to reduce sensor size, it is becoming difficult to provide a sufficient gap between the ceramic separator and the casing (or filter support cylinder). Although it is theoretically possible to reduce the diameter of the ceramic separator, there is a limitation on the ability to reduce the diameter of the ceramic separator size reduction on the assumption of securing and still maintain the basic function of the ceramic separator and prevent against shorting between the lead wires.

It is therefore an object of the invention to provide a gas sensor which can efficiently flow air through the casing while having a sufficient on-axis sectional area for a ceramic separator that allows lead wires to pass through.

SUMMARY OF THE INVENTION

In order to solve the problems described above, the invention provides a first structure of a gas sensor that includes a detection element formed in an axial form, a cylindrical casing for accommodating the detection element, and a ceramic separator in a columnar form placed in an axial direction of the casing and having a plurality of lead wire insertion holes formed penetrating therethrough in the axial direction to pass through each lead wire from the detection element, wherein the ceramic separator depicts inscribed and circumscribed circles about a geometric center of gravity of an external shape line on an arbitrary section plane (hereinafter referred to as a contour forming on-axis section plane) perpendicular to the axis and on which an external shape of the ceramic separator can be represented in a continuous single contour, wherein, if depicting a virtual reference circle positioned intermediate between the inscribed circle and the circumscribed circle, the contour forming on-axis section plane having an external shape line that in one par is positioned on an inner side of the reference circle and in other part on an outer side of the reference circle.

The structure described above essentially provides a ceramic separator having an outer shape line on a contour forming on-axis section plane that at least partly departs from a circular shape. FIG. 8 shows an example of a case where, for example, the main body portion has an outer shape line SH rendered in a squared form on the contour forming on-axis section plane. With respect to an outer shape SH, inscribed and circumscribed circles IC and OC are depicted about a geometric center of gravity, and a reference circle SC is depicted between these circles. It can be understood that the outer shape line SH is at some points within the reference circle SC and at other points outside the reference circle SC. This would be true for a shape that departs from a circular shape (polygonal, elliptical, etc.) and is not limited to only a squared shape like outer shapeline SH.

That is, in a conventional gas sensor structure, the ceramic separator, without exception, is circular in shape on a contour forming an on-axis section plane. As described earlier, there has been difficulty in expanding the gap defined with a casing or filter support cylinder inner surface. According to the invention, however, the external shape line of the ceramic separator on a contour forming an on-axis sectional plane is constructed as to depart from the traditional circular shape. This makes it possible to locally expand the gap between the outer peripheral surface of the ceramic separator and the casing or filter support cylinder inner surface. Due to this, passage of external air into the casing occurs efficiently while providing the ceramic separator with a sufficient on-axis sectional area for inserting through lead wires.

Incidentally, where the ceramic separator has, for example, a main body portion in a columnar shape and a flanged separator side support portion formed projected on an outer peripheral surface of the main body, the external shape line on the contour forming on-axis section plane may be at least one of an external shape line of the main body portion and an external shape line of the separator side support portion.

The invention also provides another gas sensor structure that includes a detection element formed in an axial form, a cylindrical casing for accommodating the detection element, a filter support cylinder provided generally coaxial to the casing over an rear end portion of the casing, a ceramic separator in an columnar form placed in an axial direction of the filter support cylinder and having a plurality of lead wire insertion holes formed penetrating therethrough in the axial direction to pass through each lead wire from the detection element, a flanged separator-side support portion formed in an outer peripheral surface of the ceramic separator, a filter arranged on a rear side of the separator-side support portion and on an rear end side of the filter support cylinder, which blocks a liquid from passing through but allows a gas to pass therethrough, and a gas communication portion formed in the separator-side support portion in the axial direction.

Incidentally, in the description of the invention above, the axial side toward the tip of the detection element is the "front side (tip side)", while the side opposite to this is a "rear side (rear end side)".

In this manner, a flanged separator side support portion is formed on an outer peripheral surface of the ceramic separator. A filter is arranged on a rear side of this separator side support portion and on a rear end side of the filter support cylinder, which blocks a liquid from passing through, but allows a gas to pass. A gas communication portion is axially formed in the separator side support portion. This allows the air introduced through the filter to be smoothly and speedily introduced to an inside of the casing through the gas communication portion axially formed in the separator side support portion. Moreover, a filter is provided which blocks liquid from passing, but allows a gas to pass through. Accordingly, where mounted, for example, on a gas discharge pipe, or the like, close to a vehicular wheel, it is possible to introduce external air even if water is sprayed onto the structure during rain or during washing of the vehicle. Accordingly, the gas sensor can be reduced in outer diameter without impeding the performance of the sensor.

The gas communication portion can form one part of a communication path for air directed from the filter to an internal tip side of the casing along the outer peripheral surface of the ceramic separator. In this manner, where the air introduced through the filter can be introduced to the internal tip side of the casing through a shortest communication path, the circulation of air as a reference gas is promoted to improve ventilation performance, enabling gas concentration detection with accuracy.

Also, according to the invention, the separator side support portion can have an external contour line on the contour forming an on-axis section plane exhibiting a polygonal shape, and the gas communication portion being formed between an inner surface of the filter support cylinder and an outer peripheral surface of the separator side support portion in a form including the external shape line. In this case, the gap between the outer peripheral surface of the separator side support portion and the inner surface of the filter support cylinder can be locally expanded, thus securing a minimum amount of communication air to the inside of the casing. Also, because the external shape line on the contour forming on-axis section plane is in a polygonal form, it is possible to provide a homogeneous air flow state with respect to a circumferential direction.

Furthermore, the gas communication portion of the invention can be formed in a flat plane or groove forming the outer peripheral surface, or in a pore form penetrating through the separator side support portion. In any case, the gas communication portion can be integrally formed during forming of the ceramic separator. Thus, manufacture can be accomplished easily and at low cost.

With respect to the gas structures described above, the following features may also be provided. On the rear end side of the casing a cylindrical filter support portion may be provided having one or a plurality of gas introducing pores formed in a wall thereof. A filter is arranged for closing the gas introducing pores in the filter support portion to block liquid from passing but to allow a gas to pass through, whereby a gas introducing structure portion is formed to introduce air into the casing through the gas introducing pores and the filter. The invention also provides that the main body part of the ceramic separator is arranged at an axially rear side of the detection element and extends to an inner side of the filter support portion, wherein a gap formed between the main body part outer peripheral surface and the filter support portion inner peripheral surface forms one part of a communication passage for the air directed through the filter to the internal tip side of the casing.

A further embodiment of the invention provides that a ceramic separator is formed with a flanged separator side support portion projecting from an outer peripheral surface of the main body part at an axially intermediate position whereby the main body part at the separator side support portion is abutted against an rear end face of the casing directly or indirectly through another member in a state that a portion axially forwardly positioned of the separator side support portion is inserted to a rear end inner side of the casing, while an axially rear portion is arranged so as to project to an outer side of the casing where the projected portion is covered by the filter support portion formed in a cylindrical form separately from the casing, and further including a gas communication portion axially formed in the separator side support portion to allow a gas to flow from the inner side of the filter support portion to an inner side of the casing.

BRIEF DESCRIPTION OF THE DRAWINGS

The invention is described in relation to the following drawings, in which like reference symbols refer to like elements, and wherein.

DETAILED DESCRIPTION OF THE PREFERRED EMBODIMENTS

Now embodiments of the invention will be described with reference to the drawings.

Figure 1:
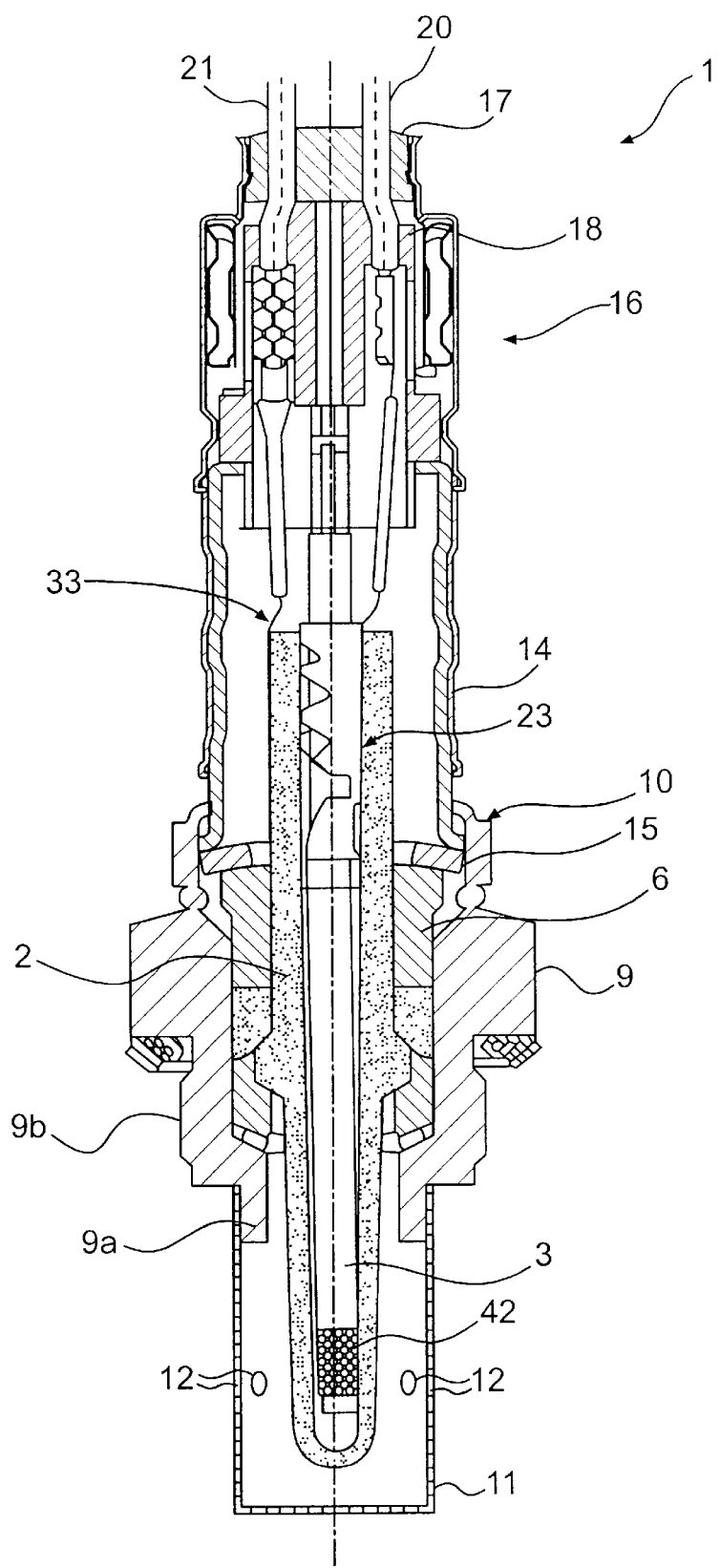
FIG. 1 is a longitudinal sectional view showing an oxygen sensor according to an embodiment of the gas sensor of the invention.

FIG. 1 shows the internal structure of an oxygen sensor according to one embodiment of the gas sensor according to the invention. The oxygen sensor 1 includes an oxygen detection element (detection element) 2 formed by a solid electrolytic member in a hollow cylindrical form having a closed end and a heating element 3. The oxygen detection element 2 is hollow and is formed of an oxygen ion conductive solid electrolyte based on zirconia or the like. A metal casing 10 is provided on an outer side of the oxygen detection element 2.

Figure 2:
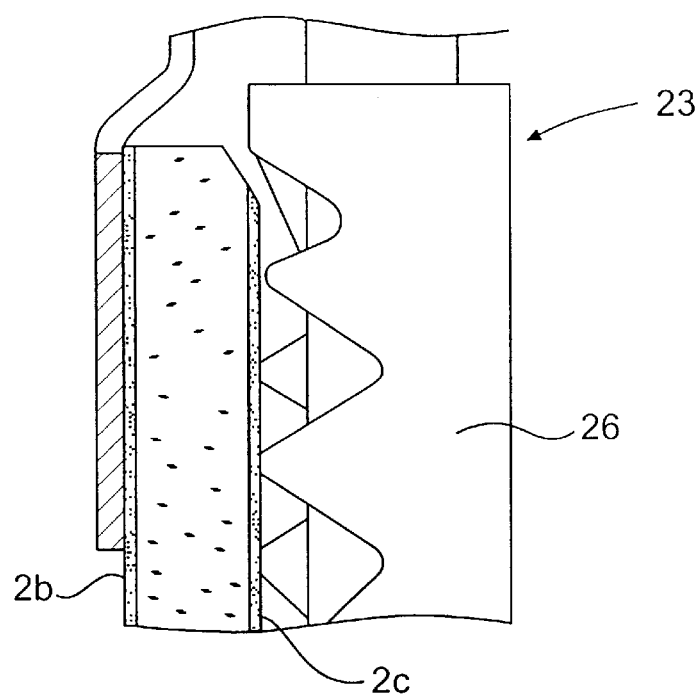
FIG. 2 is a magnified sectional view showing an oxygen detection element portion.
Figure 2:
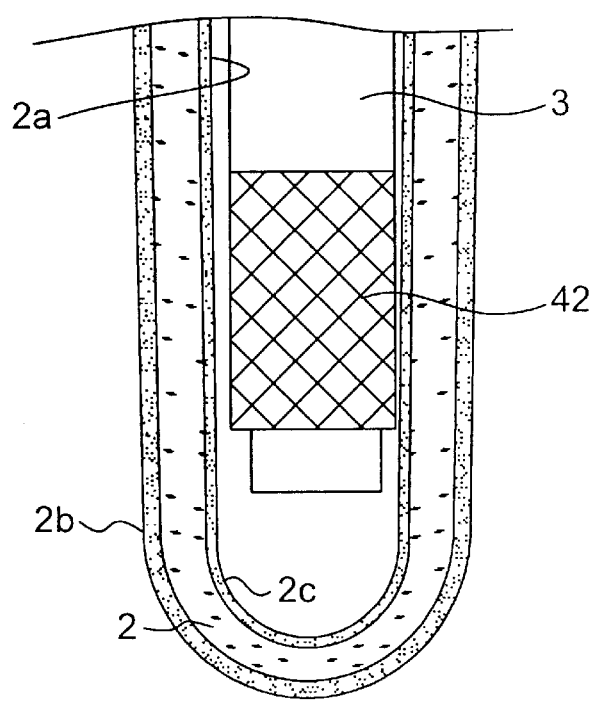

The casing 10 has main hardware 9 formed with a threaded portion 9b to mount the oxygen sensor 1 on a mount part, such as an exhaust pipe, a main cylinder 14 coupled in internal communication to one opening of the main hardware 9, and a protector 11 attached to the main hardware 9 from a side opposite to the main cylinder 14. The oxygen detection element 2 has, as shown in FIG. 2, a pair of electrode layers 2b, 2c which are porous, e.g. of Pt or a Pt alloy, to cover over almost the entire inner and outer surfaces thereof.

Referring back to FIG. 1, the main body hardware 9 at the opening on a rear side is crimped with the main cylinder 14 through a ring 15 on an insulator 6. The main cylinder 14 is fixed, by fitting it with a cylindrical filter assembly 16. The filter assembly 16 is sealed by a grommet 17 at its rear end opening. The grommet 17 is formed from rubber or the like. Inward of this, a ceramic separator 18 is provided. Lead wires 20, 21 for the oxygen detection element 2 as well as lead wires for the heating element 3 (not shown) are provided penetrating through the ceramic separator 18 and grommet 17.

Figure 3:
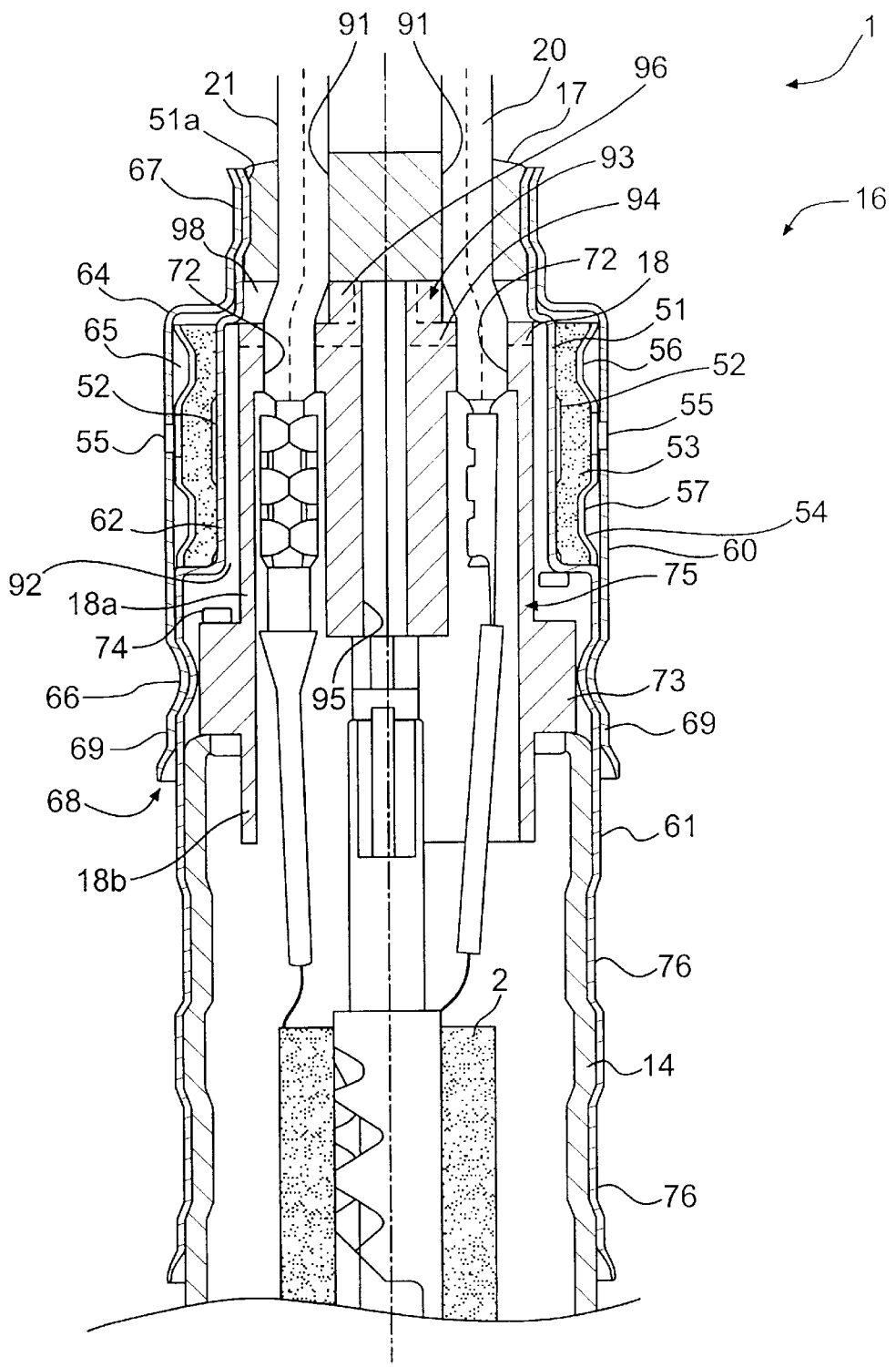
FIG. 3 is a magnified sectional view showing a portion of the oxygen sensor shown in FIG. 1.

As shown in FIG. 3, the ceramic separator 18 has a plurality of separator-side lead insertion holes 72 (lead wire insertion hole) axially formed penetrated for passing through the lead wires 20, 21, and a flanged separator-side support portion 73 formed in an axially intermediate position thereof in a form projecting from an outer peripheral surface. The ceramic separator 18 is received at its forward portion of the separator-side support portion 73 in a rear end inner face of the main cylinder 14 so that it abuts against a rear end surface of the main cylinder 14. Further, a rear portion of the separator support portion 73 is projected outward of the main cylinder 14.

Referring back to FIG. 1, one lead wire 20 for oxygen detection element 2 is electrically connected to the electrode layer 2c (FIG. 2) provided on the inner surface of the oxygen detection element 2 by way of an fixing hardware 23. On the other hand, the other lead wire 21 is electrically connected to the outer electrode layer 2b(FIG. 2) of the oxygen detection element 2 by way of another fixing hardware 33.

The oxygen detection element 2 is activated due to heating up of the heating element 3 placed inside thereof. The heating element 3 is a rod-shaped ceramic heater, and has a heating portion 42 having a resistance heat generating part (not shown) to be energized through a lead wire (not shown) thereby heating a tip (detecting section) of the oxygen detection element 2.

As shown in FIG. 3, the filter assembly 16 assumes a cylindrical shape axially coupled to the main cylinder 14 (casing 10) from a rear outer side, via filter support part 51; filter support part 51 (filter support cylinder) having an interior communicated with an outside of the main cylinder 14 and a wall formed with a plurality of gas introducing pores 52. On an outer side of the filter support part 51, a cylindrical filter 53 is provided to close the gas introducing pores 52. Further, on an outer side of the filter 53, an auxiliary filter support part 54 is provided which has a wall formed with one or a plurality of auxiliary gas introducing pores 55 and holds the filter 53 by sandwiching it with the filter support part 51. Specifically, the gas introducing pores 52 and auxiliary gas introducing pores 55 are circumferentially formed in each axially intermediate position at a predetermined interval in a corresponding positional relation to each other with respect to the filter support part 51 and auxiliary filter support part 54. The filter 53 is arranged in a manner circumferentially surrounding the filter support part 51. Incidentally, the filter 53 is in a porous fibrous structure, for example, of polytetrafluoroethylene (product name: Goatex (Japan Goatex Co. Ltd.)), which is structured as a water-repellent filter to block a liquid based on water such as water droplets from passing through but allows a gas such as air and/or water vapor to pass through. Incidentally, both the main cylinder 14 and the filter support part 51 are cylindrical in shape. Incidentally, the filter 53 is in a porous fibrous structure, for example, of polytetrafluoroethylene (product name: Goatex (Japan Goatex Co. Ltd.)), which is structured as a water-repellent filter to block a liquid based on water such as water droplets from passing through but allows a gas such as air and/or water vapor to pass through. Incidentally, both the main cylinder 14 and the filter support part 51 are cylindrical in shape.

Figure 4:
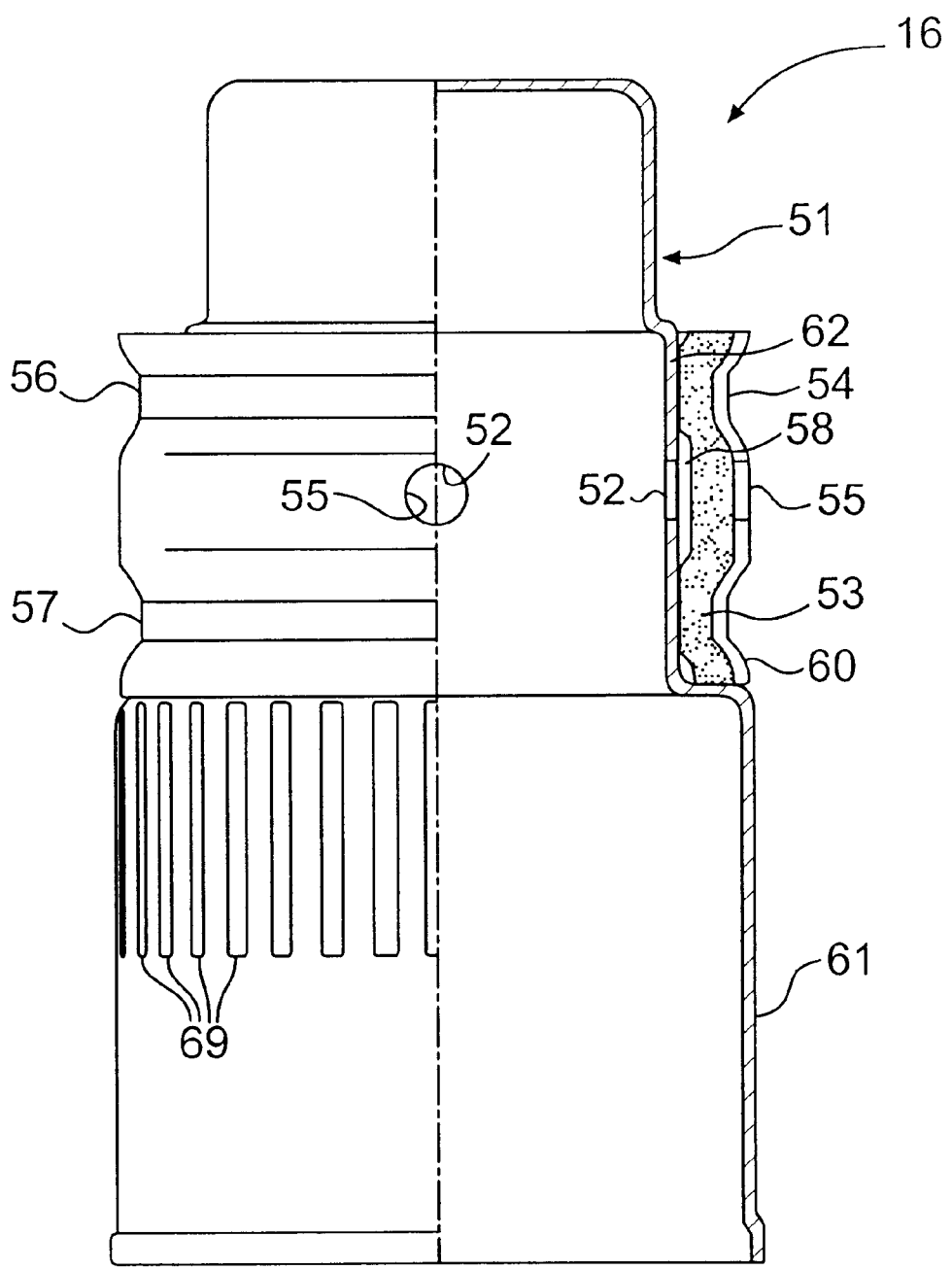
FIG. 4 is a sectional view of a filter assembly according to the invention.

As shown in FIG. 4, the auxiliary filter support part 54 has annular filter crimp portions 56, 57 (hereinafter referred merely as crimp portions 56, 57) formed at positions sandwiching a row of the auxiliary gas introducing ports 55 and respective sides of their axes. By the crimp portions 56, 57, the auxiliary filter support part 54 is coupled to the filter support part 51 through the filter 53. Also, a gap 58 is provided between an outer surface of the filter support part 51 and the filter 53. On the other hand, the filter support part 51 includes a step portion 60 formed in an axially intermediate portion to have a first portion 61 that is axially forwardly positioned with respect to the step portion 60 and a second portion 62 that is axially rearwardly positioned. The second portion 62 is formed smaller in diameter than the first portion 61. The gas introducing pores 52 are formed in a wall of the second portion 62. Further, the auxiliary filter support part 54 has an inner diameter smaller than an outer diameter of the first portion 61 of the filter support part 51.

Referring back to FIG. 3, the filter support part 51 covers the projected portion of the ceramic separator 18 extended up to an inner side of the second portion 62, and is arranged to abut at the step portion 60 against the separator-side support portion 73 through a metal elastic member 74 from an opposite side to the main cylinder 14. On the other hand, the filter support part 51 at a tip side, or at the first portion 61, is arranged to overlap, from an outer side, with the main cylinder 14 (casing 10). The overlap portion has a casing crimp portion 76 to air-tightly couple the filter support part 51 to the main cylinder 14.

The auxiliary filter support part 54 has, at its outer side, a cylindrical protect cover 64 in a manner covering over same. This protect cover 64, as show in FIG. 3, is arranged to provide a gas staying space 65, and joined by crimp portions 66, 67 to the filter support part 51. Incidentally, as shown in FIG. 4, a plurality of grooves 69 are circumferentially formed at a predetermined interval in an outer peripheral surface of the first part 61, which serve as a gas introducing part to an inside of the protect cover 64.

Referring back to FIG. 3, the ceramic separator 18 is placed such that it extends at its rear side to an inside of the filter support part 51 and at its front side to an inside of the main cylinder 14 (casing 10) with respect to an axial direction of the oxygen detection element 2. The leads 20, 21, etc. are axially inserted in the separator-side lead wire insertion hole 72. On the other hand, grommet 17 is resiliently fitted in a rear-side opening 51a of the filter support part 51 to have a seal-side lead wire insertion hole 91 for inserting the lead wires 20, 21, etc. therein, and provides sealing between an outer surface of the lead wires 20, 21, etc. and an inner surface of the filter support part 51.

The rear end face of the ceramic separator 18 is positioned axially rear to the gas introducing ports 52. The rear end is centrally formed with a gap regulating projections 96 having summit surfaces that are close contacted with a front face of the grommet 17. Due to the gap regulating projections 96, a predetermined amount of a gap 98 is given between the grommet 17 and the ceramic separator 18. Incidentally, the gap regulating projections 96 may be formed in a front face of the grommet 17 instead of the ceramic separator 18. Also, a gap 92 is provided between an inner peripheral surface of the filter support part 51 and an outer peripheral surface of the ceramic separator 18. The gas from the gas introducing port 52 is supplied into the gap 92 and further introduced into the casing 10 via a gas introducing part 93 formed in the ceramic separator 18. Specifically, the ceramic separator 18 has an axial gas-passage through-hole 95 formed separately from the separator-side lead wire insertion holes 72, and a gas-passage groove 94 formed at its rear end face that has one end communicated with the through-hole 95 and the other end opened to the outer surface of the ceramic separator 18. That is, these gas-passage through-hole 95 and gas-passage groove 94 constitute a gas introducing part 93.

Referring back to FIG. 1, the main hardware 9 is formed, at its front-side opening, with a cylindrical protector fitting portion 9a to which a cap-formed protector 11 is fitted, with a predetermined spacing, to cover a tip side (detecting section) of the oxygen detection element 2. The protector 11 is formed with a plurality of gas passing ports 12 to pass through an exhaust gas.

In the oxygen sensor 1, air as a reference gas is introduced through the filter 53 of the auxiliary filter support part 54. On the other hand, exhaust gas introduced through the gas passing ports 12 of the protector 11 comes into contact with an outer surface of the oxygen detection element 2. The oxygen detection element 2 has an oxygen concentration battery electromotive force dependent upon an oxygen concentration difference between inner and outer surfaces thereof. This oxygen concentration battery electromotive force is taken out as a detection signal of an oxygen concentration in the exhaust gas from the electrode layer $2b$, $2c$ (FIG. 2) through the lead wires 21, 20. Thus, an oxygen concentration in an exhaust gas can be detected.

Figures 14A, 14B, 14C, 14D, 14E:
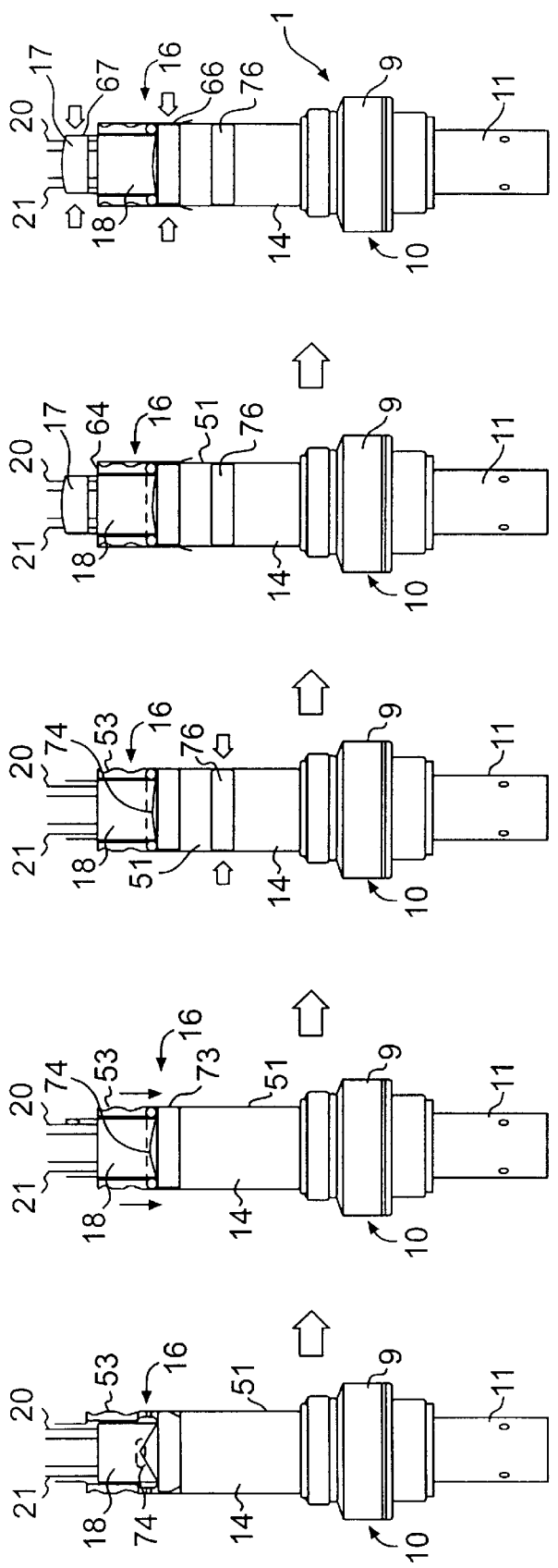
FIGS. 14(a), 14(b), 14(c), 14(d) and 14(e) illustrate a process for assembling a filter assembly according to the invention.

Incidentally, assembling a filter assembly 16 on the main cylinder 14 can be made, for example, as follows. That is, as shown in FIG. 14(a), a metal elastic member 74 is inserted in a ceramic separator 18 and further the ceramic separator 18 at its front side is inserted to a main cylinder 14. On the other hand, a filter assembly 16 having been previously assembled as shown in FIG. 4 is externally fitted at its filter support part 51 to the ceramic separator 18 and main cylinder 14, as shown in FIG. 14(a). Incidentally, an oxygen detection element 2, heating element 3, etc. (FIG. 1) are previously assembled in the main cylinder 14. The lead wires 20, 21, etc. of them are passed through the separator-side lead wire insertion holes 72 (FIG. 3) of the ceramic separator 18 and allowed to extend from a rear end opening of the filter support part 51.

Subsequently, as shown in FIG. 14(b), the main cylinder 14 and filter assembly 16 are applied by utilizing an axial compression force. This causes the metal elastic member 74 to be compressed and deformed between the filter support member 51 and the separator-side support portion 73 of the ceramic separator 18, to cause an urging force for clamping the ceramic separator 18 between the main cylinder 14 and the filter support portion 51. While keeping this state, a casing crimp portion 76 is formed in the filter support part 51 and main cylinder 14, for joining them as shown in FIG. 14(c). Then, as shown in FIG. 14(d), the filter support portion 51 at its rear end opening is inserted by a rubber grommet 17 and further covered by a protect cover 64, and crimp portions 66 and 67 are formed as shown in FIG. 14(e), thus completing the assembling for the oxygen sensor 1.

Figure 5A:
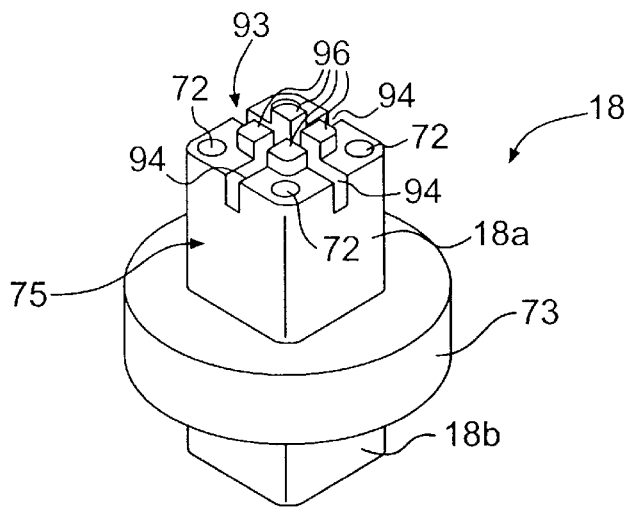
FIGS. 5(a), 5(b) and 5(c) are perspective views showing a ceramic separator together with its modifications according to the invention.
Figure 7A:
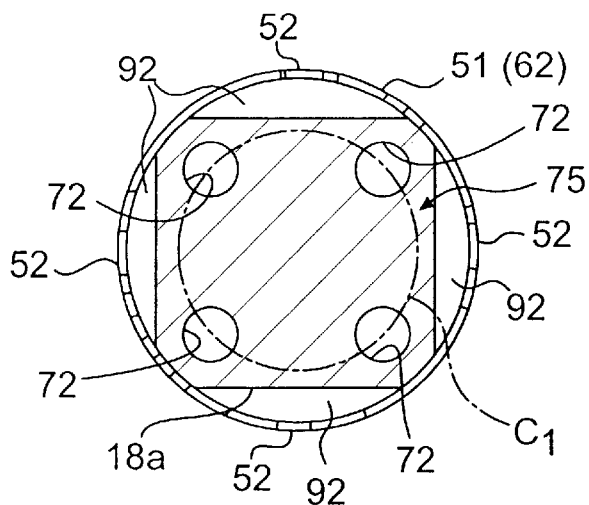
FIGS. 7(a), 7(b) and 7(c) are sectional views showing a shape on a contour forming on-axis section plane of a main body part of the ceramic separator together with its modification.

Next, as shown in FIG. 5(a), the ceramic separator 18 has a main part 75 that is in a shape at least party different from a circular shape, specifically a square in on-axis sectional shape. In this embodiment, the main body part 75 (hereinafter, see also FIG. 3) comprises two parts, i.e. a part 18a to be inserted in the second section 62 of the filter support part 51 (hereinafter referred to as "first part") and a part 18b to be inserted to an inner side of the main cylinder 14 (hereinafter referred to as "second part"). The square columnar form in at least the first part 18a makes it possible to secure a relatively large gap 92 between the same and an inner surface of the filter support part 51, as shown in FIG. 7(a), thereby ensuring smooth air flow. Incidentally, the second part 18b of the main body part 75 may be formed in a circular form. Also, although in FIG. 5(a) the gap regulating projections 96 are also formed in a square columnar form, this may be formed in a circular cylinder or other forms.

Here, as shown in FIG. 3 the oxygen sensor 1 of the present embodiment has, on a rear end outer side of the casing 10, a cylindrical filter support portion 51 (filter support cylinder) formed with a gas introducing pores 52 in a wall thereof and covered coaxially over the casing 10 from a rear side. The filter assembly 16 is arranged with a filter 53 to block a liquid from passing, but allows a gas to pass through, in a manner closing the gas introducing pores 52 of the filter support part 51. Thus, a gas introducing structure part is formed to introduce external air into the casing 10 through the gas introducing pores 52 and filter 53. Also, the main body part 75 of the separator 18 is arranged such that the first part 18a on the rear side extends to an inside of the filter support part 51. Further, the gap 92 given between an outer peripheral surface of the first part 18a (main body part 75) and an inner peripheral surface of the filter support part 51 serves to form a part of a communication passage for external air to be introduced to an inside of the casing 10 through the filter 53. Because this structure allows external air to flow from the filter 53 side into the sufficiently broad gap 92, the external air flow within the casing 10 can be made with further smoothness.

Also, the main body part 75 of the ceramic separator 18 at its rear end face is positioned rear of the gas introducing ports 52 provided in the filter support part 51, and the main body part 75 has the gas-passage through-hole 95 formed axially penetrating therethrough. In this case, the external gas introduced through the gas introducing pores 52 is to be guided to a tip portion of the detection element 2 through the gap 92. The flow path is as follows. That is, the introduced external air flows from the gap 92 to a rear side of the ceramic separator 18, and further through the gas-passage through-hole 95 to the internal tip side of the detection element 2. The polygonal shaped main body part 75 (its first part 18a) of the ceramic separator 18 realizes smooth gas passage through the gap 92.

Here, as shown in FIG. 5(a) and FIG. 3 the ceramic separator 18 is formed with four separator-side lead wire insertion holes 72 which are arranged such that their centers are positioned on a hypothetical circle C1 (separator-side pitch circle) in order to pass through the lead wires extended from the oxygen detection element 2 and heating element 3. Also, the gas-passage through-hole 95 is formed in a region surrounded by the four separator-side lead wire insertion holes 72 in a central part of the ceramic separator 18. Further, the gas-passage groove 94 is formed in a cross form in a position where there is no interference with the four separator-side lead wire insertion holes 72. The grommet 17 at its front end face contacts with the ceramic separator 18, in an opening position of the gas-passage through-hole 95. However, because the gas-passage groove 94 is formed, the air is not prevented from flowing from the gap 92 to the gas-passage through-hole 95.

Also, in FIG. 3, the grommet 17 is formed with a seal-side lead wire insertion hole 91 positioned on a seal-side pitch circle. The above-mentioned separator-side pitch circle (diameter D1) and the seal-side pitch circle (diameter D2) are set such that one is greater in diameter than the other. For example, in FIG. 3 a relationship D1>D2 is given. As shown in FIG. 5(a), the gap regulating projections 96 are formed in an area positioned at inner side of the separator-side lead wire insertion holes 72 arranged on a separator-side pitch circle. In this case, although the lead wires are caused by bending between the grommet 17 and the ceramic separator 18, a gap 98 is provided based on the gap regulating projection 96 between the grommet 17 and the ceramic separator 18. Consequently, there is less possibility of causing such trouble that the lead wire be strongly bent resulting in damage or disconnection during assembling the sensor 1. Also, even if the grommet 17 is acted on by an axial pressing force, the grommet 17 is stopped from moving by the gap regulating projections 96. Thus, the gap amount is hardy changed and the lead wires are prevented from causing strong bending thereon.

Figure 7B:
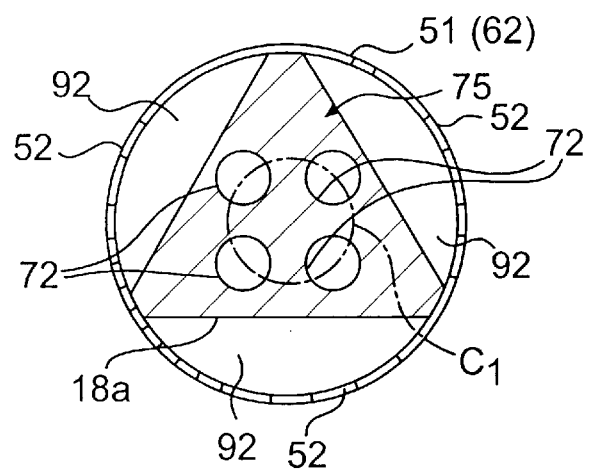
Figure 7C:
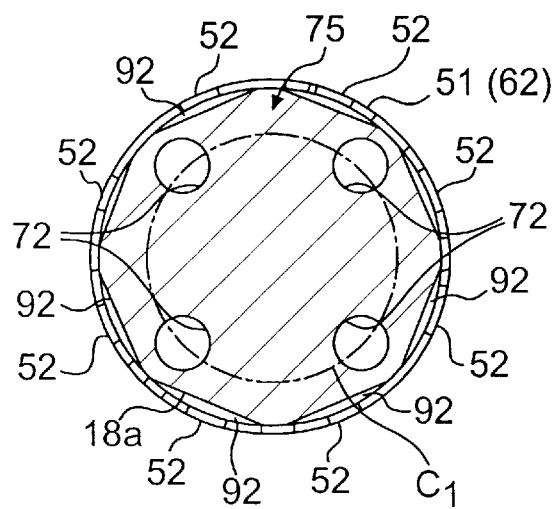
Figure 8:
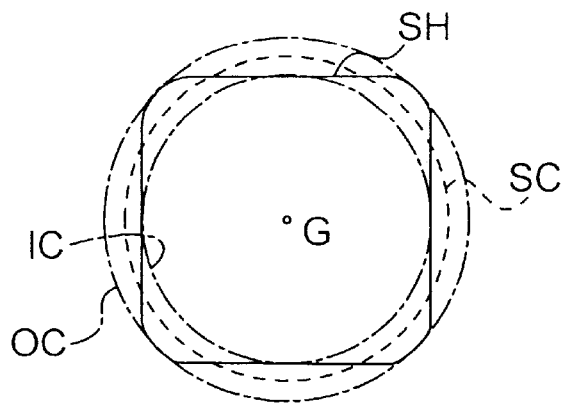
FIG. 8 is a sectional view illustrating a feature of an external line shape of a contour forming an on-axis section plane shape of the main body part.

FIGS. 7(a), 7(b) and 7(c) show examples whereby the main body part 75 of the ceramic separator 18 is made in various polygonal shapes of an on-axis section. FIG. 7(a) is in a square columnar form as already shown, FIG. 7(b) is in a triangular columnar form and FIG. 7(c) is in a octagonal column. As can be understood these figures, where the main body part 75 is made in a hexagonal form in on-axis shape, a circular shape is approached by increasing the number of sides. This, however, does not provide the significant effect of expanding the gap 92 between it and the filter support portion 51 (second part 62 thereof). On the other hand, as for the separator-side pitch circle, where the lead wires exist, for example, four in number, the triangular columnar form of FIG. 7(b) excessively reduces the pitch circle size. Accordingly, it can be said that the square columnar shape is preferred as a main body part 75 form for the ceramic separator 18 which can secure a sufficiently great pitch circle while securing a sufficient gap 92.

In this case, if gas introducing pores 52 are provided corresponding to the on-section sides of the main body part 75, it is possible to efficiently introduce a gas to the gap 92 between the ceramic separator 18 and the filter support part 51. Also, if chamfer or round is given to each edge, such trouble as marring to the casing is relieved during assembling.

Figure 9A:
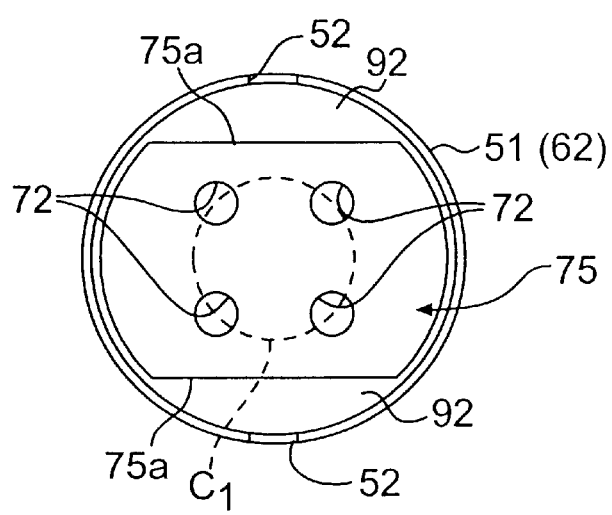
FIGS. 9(a) and 9(b) are sectional views showing modifications on the main body part of the contour forming an on-axis section plane shape.
Figure 9B:
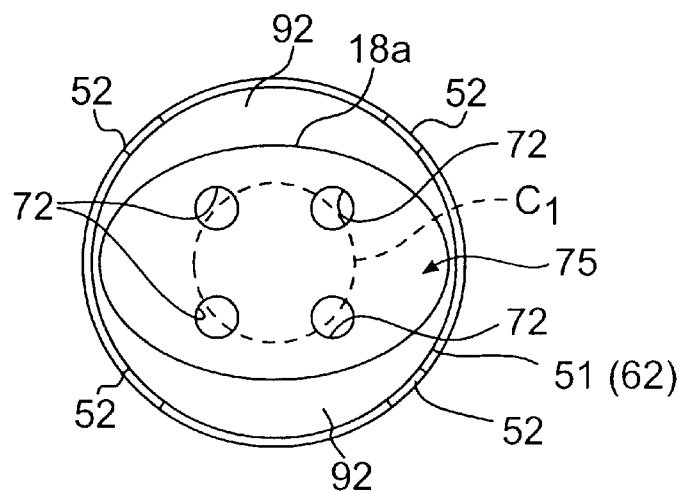

FIGS. 9(a) and 9(b) show examples whereby the main body part 75 in an on-axis section is made in a form other than polygonal in shape. In FIG. 9(a), cut-outs are oppositely provided with respect to an axis of the circular on-axis section thereby forming a pair of flat portions 75a, 75a that are parallel with each other. On the other hand, FIG. 9(b) is an example of an elliptic shape on the on-axis section.

Figure 5B:
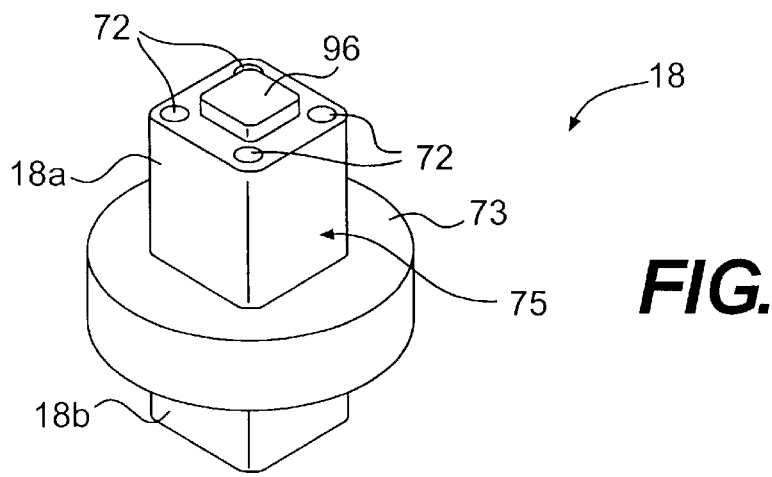
Figure 6:
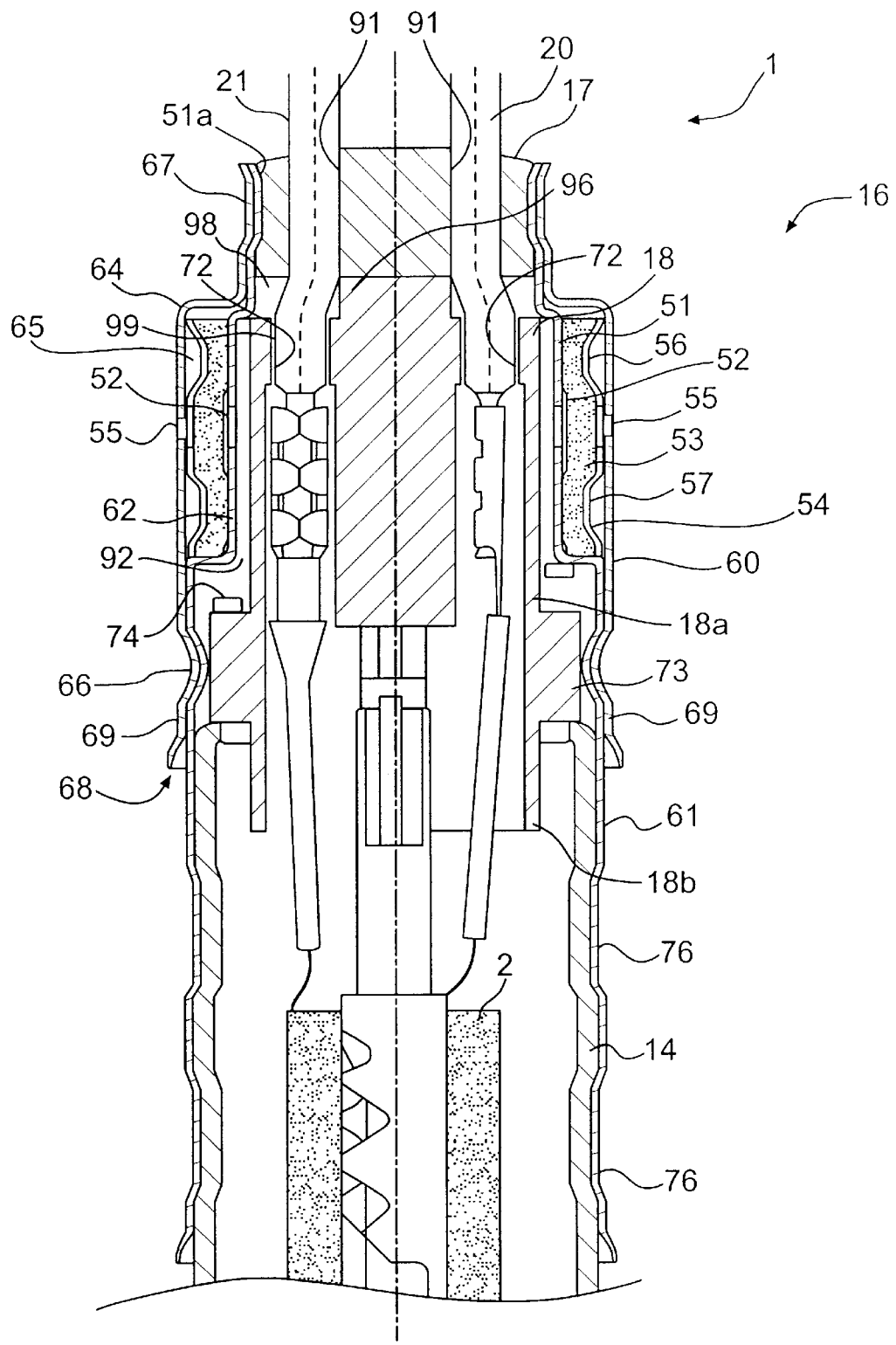
FIG. 6 is a magnified sectional view of an oxygen sensor incorporating the ceramic separator shown in FIG. 5(b)

The ceramic separator 18 shown in FIG. 5(b) is not formed with a gas introducing groove 94 or gas introducing part 93 including gas-passage through-hole 95, etc. Also, a gap regulating projection 96 is formed at a center on a rear end face of the ceramic separator 18. In this case, as shown in FIG. 6, a gas-passage gap 99 (see FIG. 6) is circumferentially formed between the separator-side lead wire insertion hole 72 and the lead wires 20, 21, etc. to provide a structure that the air introduced through the gas introducing pores 52 is guided from the gap 72 through the gas-passage gap 99 to the detection element 2. This omits formation of a gas introducing part 93. Further, there is no necessity of forming a groove 94 or the like that extends between the gap regulating projections 96 shown in FIG. 5(a), simplifying the shape and facilitating ease of manufacture.

Figure 5C:
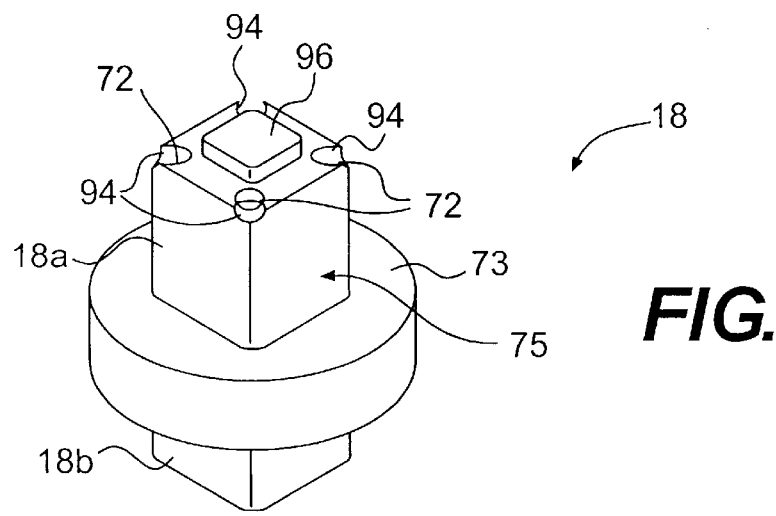

Incidentally, for the ceramic separator 18 shown in FIG. 5(b), gas-passage grooves 94 may be formed as shown in FIG. 5(c) that are directed from end-face outer peripheral edges thereof toward the respective separator-side lead wire insertion holes 72. This further makes the air flow to the detection element 2 (FIG. 1) within the casing more effective.

Figure 10A:
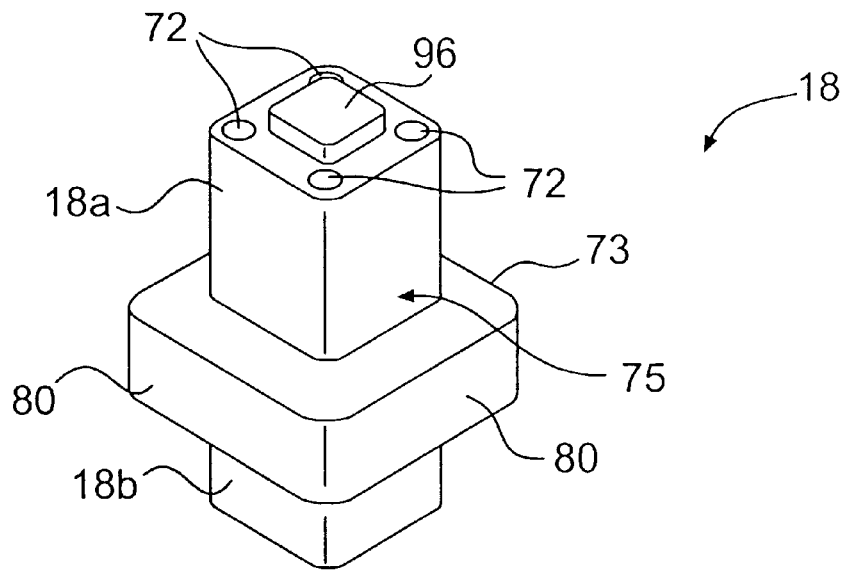
FIGS. 10(a) and 10(b) are perspective and cross-sectional views showing a first modification to the separator side support portion of the ceramic separator and a view for explaining a feature of an external line shape of the contour forming on-axis section plane shape of the separator side support portion.
Figure 10B:
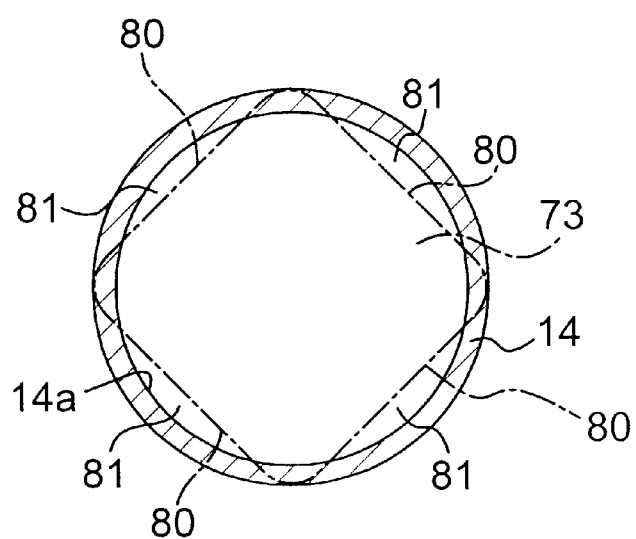

A modification to the separator-side support portion 73 of the ceramic separator 18 will be shown in FIGS. 10(a) to 13 and FIG. 15. The ceramic separator 18 shown in FIG. 10 is an example of the outer peripheral surface of the flanged separator-side support portion 73 positioned inward of an opening inner edge 14a of the main cylinder 14 (casing 10), whereby retraction passages 80 (gas communication portion) are axially formed to partially eliminate a state of shielding an opening by the separator-side support portion 73 and allow air flow to an interior of the main cylinder 14. The retraction passage 80 is formed in a flat surface form. Due to this, a comparatively large gap 81 is formed between an opening inner edge 14a of the main cylinder 14 and an outer edge of the separator-side support portion 73, thus securing further smooth gas flow. The separator-side support portion 73 herein has, at its outer peripheral surface, a plurality of the retraction passages 80 formed in series in a circumferential direction, thus providing a polygonal exterior shape (square in the present embodiment). This enables a gas flow state with greater evenness with respect to a circumferential direction of the separator-side support portion 73.

Figure 11:
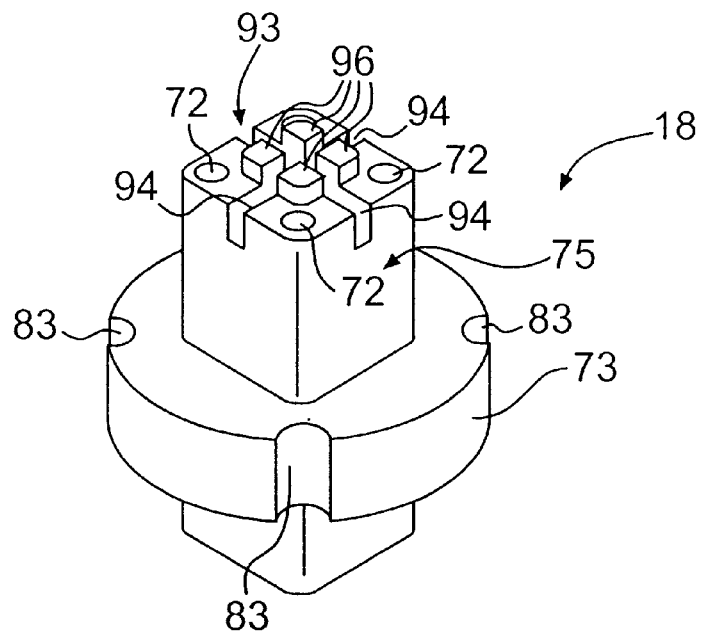
FIG. 11 is a perspective view showing a second embodiment of the invention.
Figure 12:
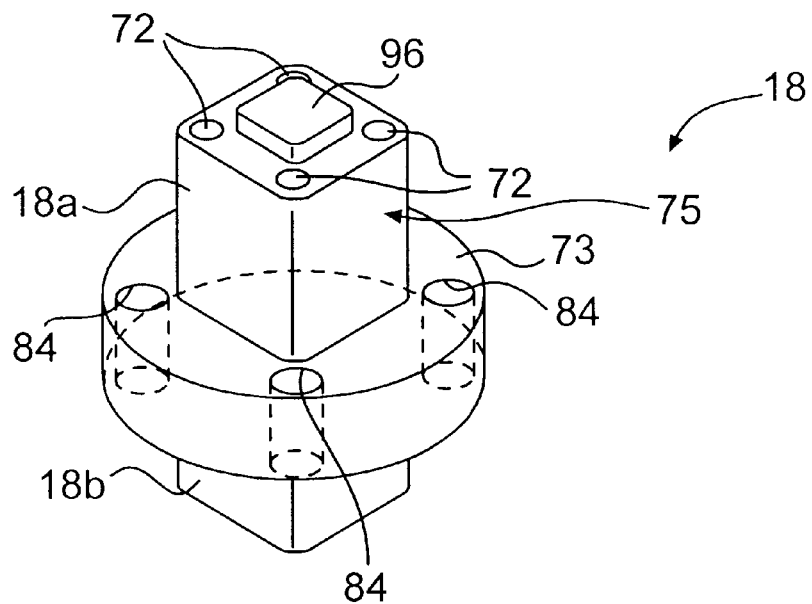
FIG. 12 is a perspective view showing a third embodiment of the invention.
Figure 13:
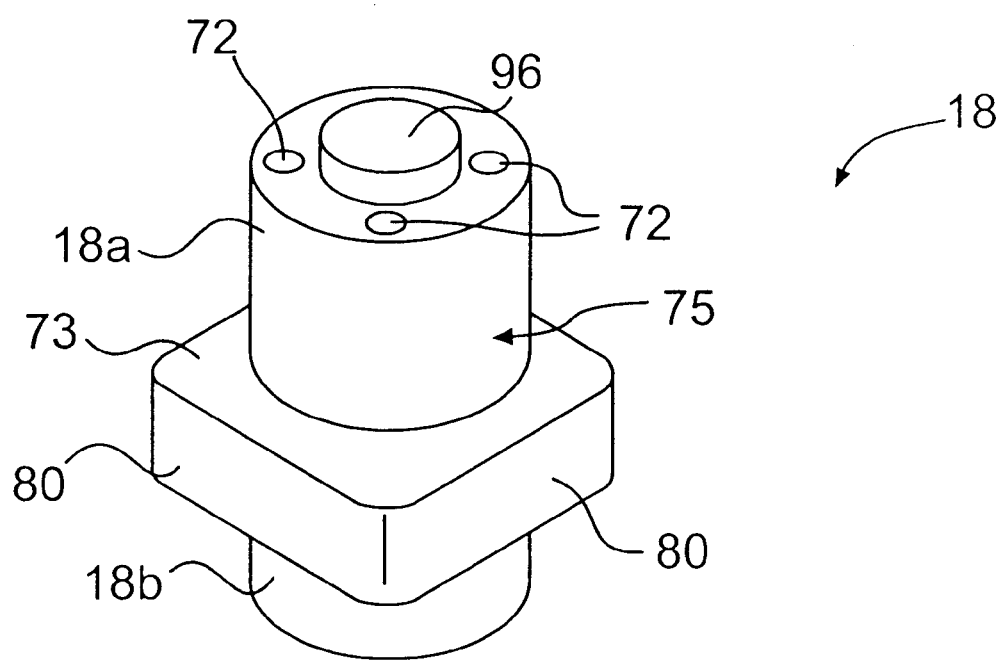
FIG. 13 is a perspective view showing a fourth embodiment of the invention.

Incidentally, grooved retraction passages 83 (gas communication portion) may be formed in the outer peripheral surface of the separator-side support portion 73, as shown in FIG. 11. Also, FIG. 12 shows an example having air-passage holes 84 formed axially penetrating through the separator-side support portion 73, in place of the retraction passages. In any example, the retraction passages 83 or the air-passage holes 84 (gas communication portion) are formed in a plurality at a predetermined interval in the circumferential direction of the separator-side support portion 73. Incidentally, where the retraction passage or air-passage holes as above are formed in the separator-side support portion, the main body part 75 of the ceramic separator 18 may be structured without particularly forming axially-penetrating air passages (e.g. air-passage groove 94 or air-passage through-hole in FIG. 3 or air-passage gap 99 in FIG. 6). Further, the main body part 75 of FIG. 10(a) may be formed in a circular cylinder as shown in FIG. 13.

Figure 15:
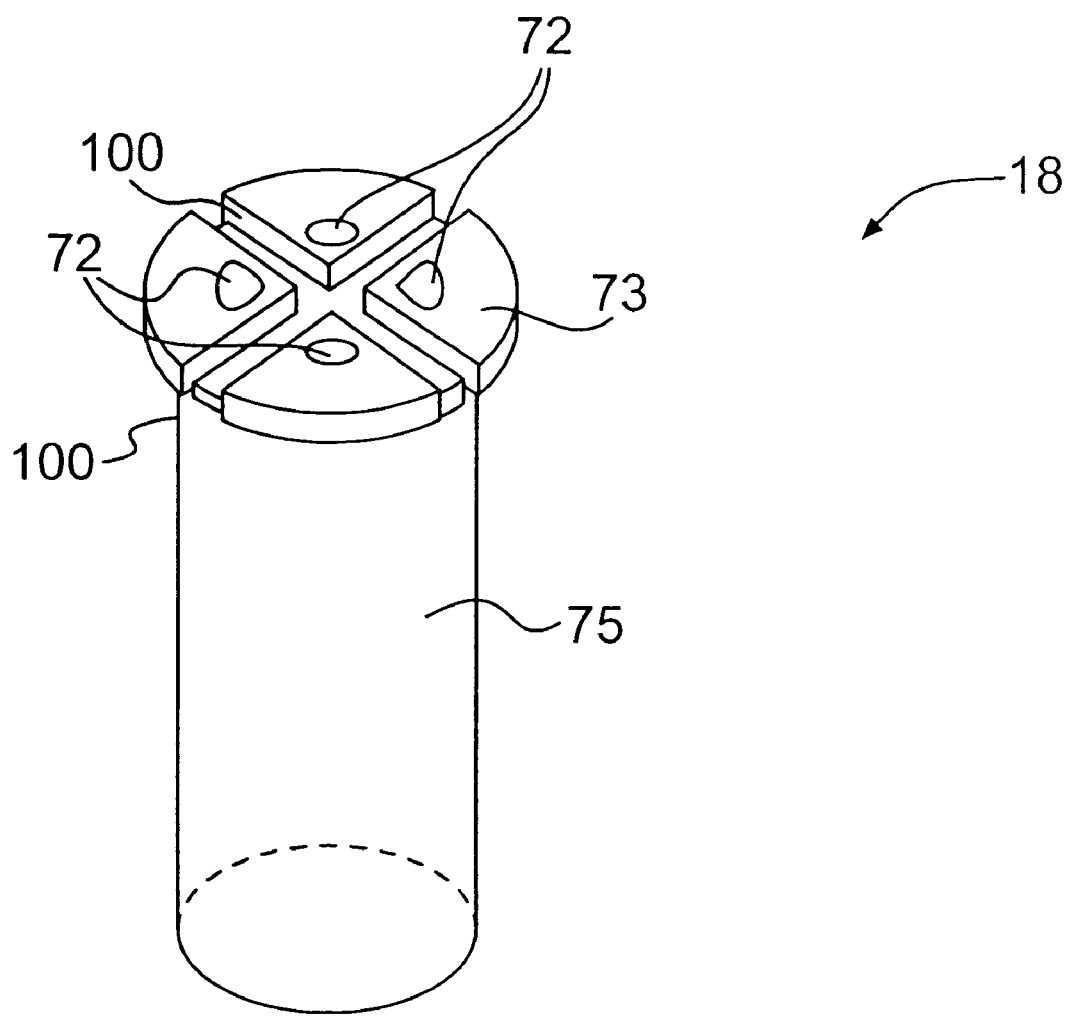
FIG. 15 is a perspective view showing a fifth embodiment of the separator side support portion of the ceramic separator according to invention.

The ceramic separator 18 shown in FIG. 15 is formed with flanged separator-side support portions 73 in a form projecting in one body fashion over the entire periphery at outer peripheral surface thereof on an axially rear side. The ceramic separator 18 has, at a position without interfering with four separator-side lead wire insertion holes 72, gas passage grooves 100 (gas communication portion) formed in a cross form in directions perpendicular to an axis on a rear end surface. Each gas passage groove 100 extends reaching the rear end outer periphery from which it changes in direction and extends toward an axially front side along an outer periphery of the separator-side support portion 73.

Figure 16:
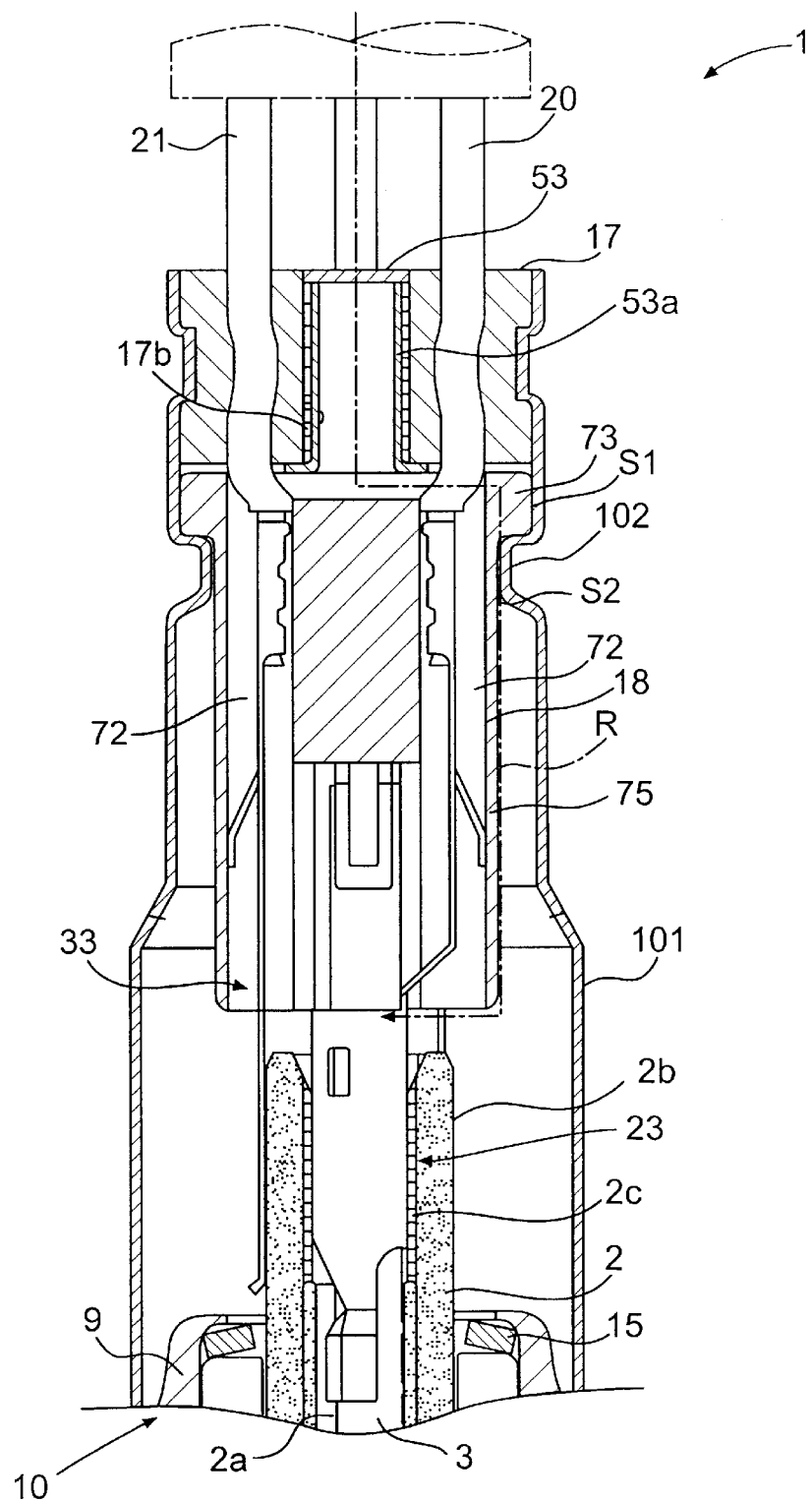
FIG. 16 is a magnified sectional view of an oxygen sensor using the ceramic separator shown in FIG. 15.

FIG. 16 shows one example of an oxygen sensor incorporating the ceramic separator of FIG. 15. A cylindrical outer cylinder member 101 (filter support cylinder) at an axially front side is formed large in diameter and fitted over a main hardware 9 (casing 10). On the other hand, the outer cylinder member 101 at an axially rear side is formed small in diameter and accommodates therein the ceramic separator 18. A grommet 17 is fitted in a rear end opening. The outer cylinder member 101 has an outer cylinder-side support portion 102 receiving and supporting the separator-side support portion 73 of the ceramic separator 18. The grommet 17 has a center through-hole 17b formed at the radial center. This center through-hole 17b receives a filter 53. The filter 53 has an air permeable surface provided in a rear end surface, and a cylindrical peripheral portion internally fitted with cylindrical filter support hardware 53a.

In the oxygen sensor 1 of FIG. 16, air as a reference gas is introduced to an inner surface (internal electrode layer 2c) of the oxygen detection element 2 through the air permeable end surface→the air passage groove 73 of the ceramic separator 18→the radial gap S1, S2 between the outer cylinder member 101 and the ceramic separator 18→hollow portion 2a (see arrow R in FIG. 16). Incidentally, in FIG. 16, the parts common to those of FIG. 3 or 6 are denoted by the same reference characters, omitting explanation thereof.

In the each case of FIGS. 10(a) to 13 and FIG. 15, the gas communication portion (retracted passage portion 83, air passage hole 84 or air passage groove 100) is provided in plurality along a circumferential direction at a predetermined interval and formed in an axial direction. Accordingly, this gas communication portion forms part of a passage for the air directed from the filter to an internal tip of the casing along the outer peripheral surface of the ceramic separator 18. Incidentally, where a gas communication portion is formed in the separator-side support portion 73 as above, a gas communication portion (e.g. the air passage groove 94 or air-passage through-hole 95 in FIG. 3 or air passage gap 99 in FIG. 6) is not structured which axially penetrate through the main body part 75 of the ceramic separator 18 (e.g. see FIG. 15 and FIG. 16).

The sensor structures as explained above are applicable similarly to the gas sensors other than the oxygen sensors, e.g. HC sensors or NOx sensors.

While the invention has been described in conjunction with specific embodiments thereof, it is evident that many alternatives, modifications and variations will be apparent to those skilled in the art. Accordingly, the preferred embodiments of the invention set forth herein are intended to be illustrative, not limiting. Various changes may be made without departing from the spirit and scope of the invention as defined in the following claims.

What is claimed is:

1. A gas sensor, comprising:

a detection element having a detection element longitudinal axis;

a cylindrical casing for accommodating the detection element, and a ceramic separator having a separator longitudinal axis and placed within the casing and having a plurality of lead wire insertion holes formed therethrough along the separator longitudinal axis and each adapted to pass a lead wire from the ceramic separator to the detection element, and wherein the ceramic separator having a geometric center, the ceramic separator further defining inscribed and circumscribed circles with respect to a cross-section of the ceramic separator and disposed about the geometric center, the cross-section of the ceramic separator forming an on-axis section plane, the plane defining a perimeter of the ceramic separator and disposed perpendicular to the separator longitudinal axis, wherein an intermediate circle is disposed between the circumscribed and inscribed circles within the plane, wherein the perimeter of the ceramic separator is disposed in part inside the intermediate circle and in part outside the intermediate circle.

2. The gas sensor according to claim 1, wherein the perimeter of the ceramic separator defines a polygonal shape.

3. The gas sensor according to claim 1, wherein the inscribed and circumscribed circles are disposed about a center of gravity of the ceramic separator.

4. A gas sensor, comprising:

a detection element having a detection element longitudinal axis;

a cylindrical casing for accommodating the detection element and having a rear end portion;

a filter support cylinder provided generally coaxial to the casing over the rear end portion of said casing;

a ceramic separator, having a first portion with a first diameter and a central separator longitudinal axis, placed within said filter support cylinder and having a plurality of lead wire insertion holes formed therethrough along the separator longitudinal axis and each adapted to pass a lead wire from the ceramic separator to the detection element, and a second portion having a second diameter larger than the first diameter and forming a flanged separator-side support portion at one end of the first portion;

a filter arranged axially rearward of said separator-side support portion on the filter support cylinder, that blocks passage of a liquid but not a gas; and a gas communication portion formed in the separator-side support portion parallel to the separator longitudinal axis.

5. The gas sensor according to claim 4, wherein the gas communication portion forms a first flow path for air directed from the filter to an internal tip side of the casing along an outer peripheral surface of said ceramic separator.

6. The gas sensor according to claim 4, wherein the separator side support portion includes a perimeter defining a polygonal shape, and wherein said gas communication portion is defined by an inner surface of said filter support cylinder and an outer peripheral surface of said separator side support portion.

7. The gas sensor according to claim 4, wherein said gas communication portion is formed in a flat plane or groove form in said outer peripheral surface of said separator side support portion.

8. A gas sensor according to claim 4, wherein said gas communication portion is defined by a pore penetrating through said separator side support portion.

* * * * *